United States Patent [19]
Lehoux et al.

[11] Patent Number: 6,144,801
[45] Date of Patent: Nov. 7, 2000

[54] PERFUME DIFFUSER

[75] Inventors: Jannick Lehoux, Thuit-Signol; Corinne Gomez, Louviers, both of France

[73] Assignee: Produits Berger S.A., France

[21] Appl. No.: 09/367,922

[22] PCT Filed: Feb. 27, 1998

[86] PCT No.: PCT/FR98/00391

§ 371 Date: Sep. 20, 1999

§ 102(e) Date: Sep. 20, 1999

[87] PCT Pub. No.: WO98/37922

PCT Pub. Date: Sep. 3, 1998

[30] Foreign Application Priority Data

Feb. 28, 1997 [FR] France .................................. 97 02451

[51] Int. Cl.$^7$ ................................................ A61M 16/00
[52] U.S. Cl. ...................................... 392/390; 239/135
[58] Field of Search ................................ 392/390, 391, 392/394, 395; 239/34, 38, 44, 45, 135, 136; 122/366; 422/125, 126; 261/DIG. 65

[56] References Cited

U.S. PATENT DOCUMENTS

| 888,415 | 5/1908 | Barber, Sr. | 239/136 |
|---|---|---|---|
| 2,741,813 | 4/1956 | Rubin | 422/305 |
| 2,742,342 | 4/1956 | Dew et al. | 422/305 |
| 3,948,445 | 4/1976 | Andeweg | 239/53 |
| 5,903,710 | 5/1999 | Wefler et al. | 392/392 |

*Primary Examiner*—Sang Paik
*Attorney, Agent, or Firm*—Bachman & LaPointe, P.C.

[57] ABSTRACT

The invention concerns a perfume diffuser comprising: a first conducting element arranged to receive part of the heat generated by the heat source, and to transmit by heat conduction the heat received; a second conducting element separated from the first element and arranged to be in contact with the perfumed substance; a third heat conducting element connected to the first conducting element and to the second conducting element so as to communicate by thermal conduction to the second element the heat transmitted by the first conducting element.

15 Claims, 2 Drawing Sheets

U.S. Patent    Nov. 7, 2000    Sheet 1 of 2    6,144,801
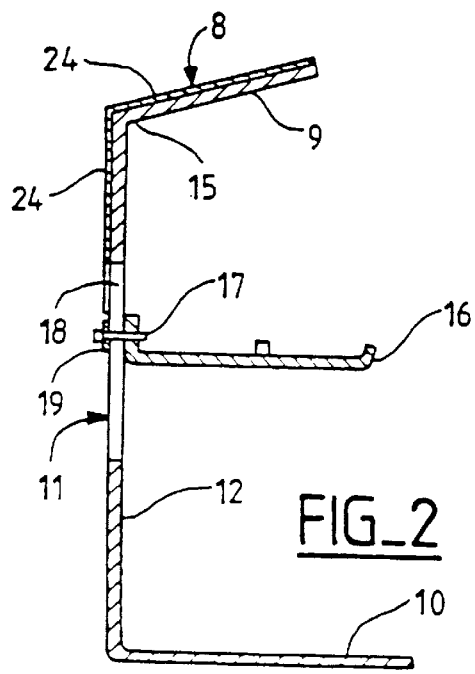
FIG_2
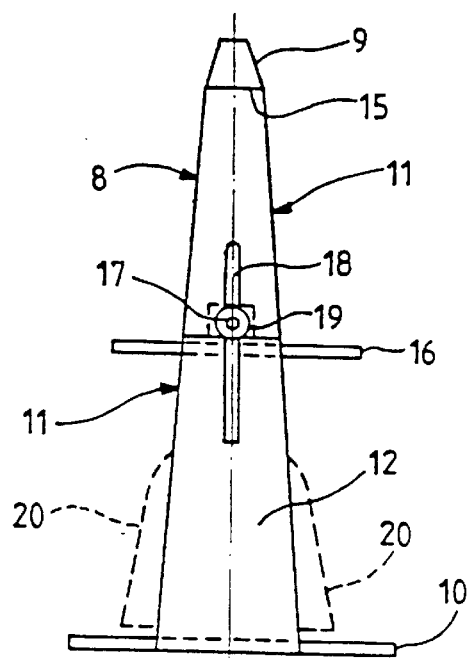
FIG_3
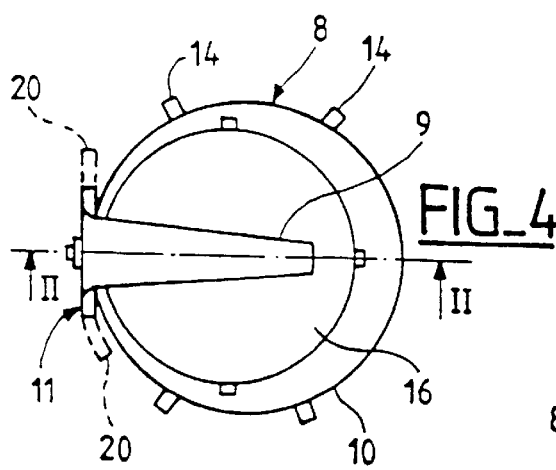
FIG_4
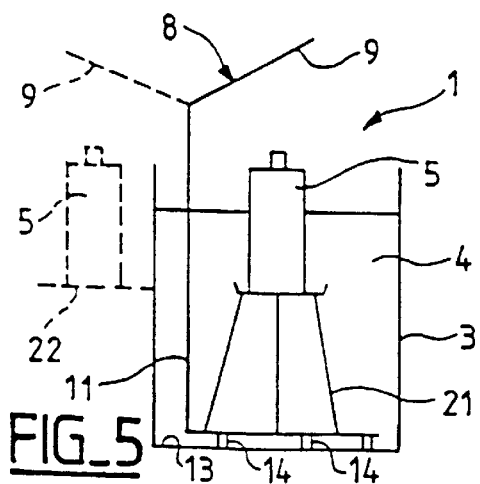
FIG_5
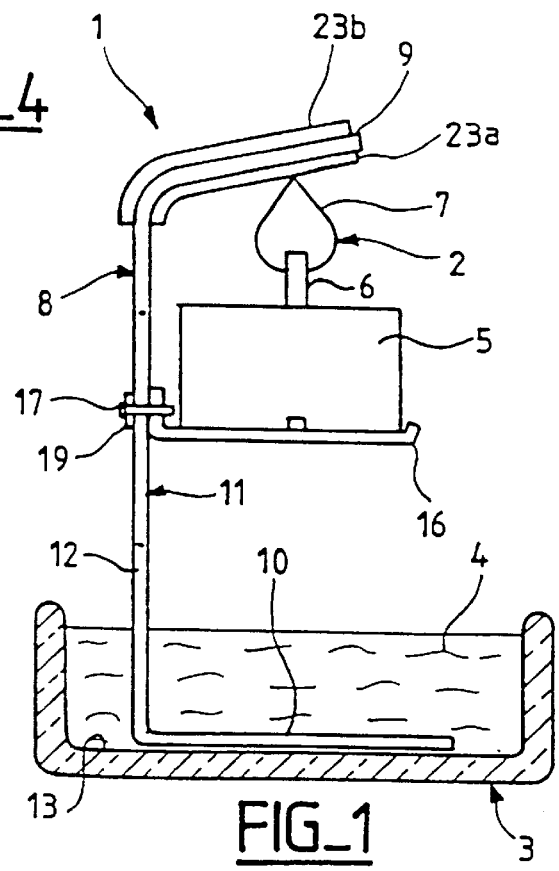
FIG_1

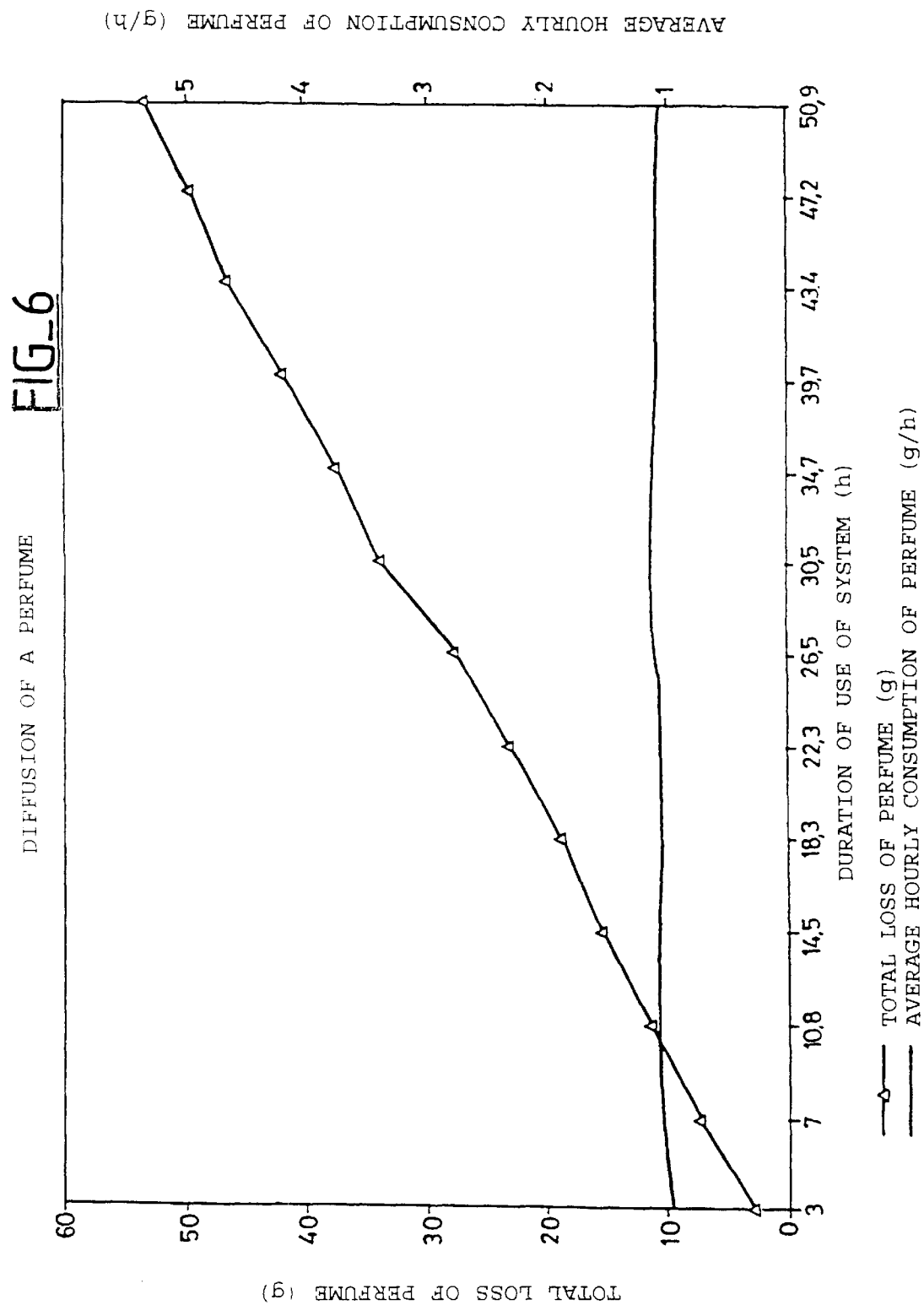

PERFUME DIFFUSER

BACKGROUND OF THE INVENTION

The present invention concerns a perfume diffuser and a system for diffusing a perfume including a perfume diffuser in accordance with the present invention.

In what follows, the diffusion of a perfume covers both the evaporation of a perfume or a perfumed substance in the form of a liquid or gel and the sublimation of a perfume or a perfumed substance in the form of a solid.

The perfume burner is a prior art perfume evaporator adapted to cooperate with a source of heat and with means adapted to receive or to constitute a container containing a substance adapted to diffuse a perfume on evaporating or sublimating, the diffuser and these means being adapted to transmit to said substance a portion of the heat produced by said source.

In a conventional configuration of the perfume burner, the source of heat is a small candle which is placed under the container, which generally contains a liquid adapted to evaporate a perfume, and which heats the container to heat said substance so that it evaporates.

The above perfume burner has a number of disadvantages. Variation of the distance between the flame and the perfume makes it impossible to adjust the temperature of the substance adapted to diffuse said perfume during use of the perfume burner. More particularly, it is very difficult to maintain the temperature of this substance in the temperature range from approximately 40° C. to approximately 65° C., which is the ideal temperature range for diffusing a perfume. The difficulty of adjusting the temperature of the substance makes it difficult to adjust the speed of diffusion of the perfume. The temperature reached during evaporation of the perfumed substance is above 65° C., which limits the choice of perfumes and reduces their olfactory quality. The capacity of the reservoir containing the perfumed substance is limited and obliges the user to refill it frequently to obtain continuous operation over several hours (the life of a candle, for example).

The whole of the perfume burner is heated, and this can produce sensations of burns.

It is not always easy to obtain access to the place for the candle.

What is more, given that the candle must be placed under the container containing the substance, the flame of the candle is largely invisible and is therefore difficult to use to create a warm and peaceful ambience, like an ordinary candle.

SUMMARY OF THE INVENTION

The aim of the present invention is to remedy the drawbacks of prior art perfume diffusers and to propose a perfume diffuser of the aforementioned type which is simple and economical, which achieves a relatively regular speed of diffusion of the perfume and which, if a flame is used as the heat source, makes the flame clearly visible.

The above perfume diffuser must additionally be capable of being integrated into all types and styles of systems for diffusing a perfume without risk of burns.

In accordance with the invention, the perfume diffuser of the aforementioned type is characterized in that it includes:

a first heat conducting element adapted to receive a portion of the heat produced by said source of heat and to transmit the heat received by thermal conduction;

a second heat conducting element separated from the first element and adapted to be in contact with said substance; and a third heat conducting element connected to the first conducting element and to the second conducting element so as to communicate the heat transmitted by the first conducting element to the second conducting element by thermal conduction;

the first and/or third conducting elements being thermally insulated over at least a portion of their outside surface, if necessary.

The presence of the three heat conducting elements enables separate adjustment of the heat received by the first conducting element, the heat transmitted from the first conducting element to the third conducting element and finally the heat transmitted by the first conducting element to the substance adapted to diffuse a perfume.

It is therefore possible to design these three heat conducting elements in a manner that achieves a substantially constant temperature of the substance adapted to diffuse the perfume.

If the source of heat is a flame, the perfume diffuser enables the flame to be positioned so that it is visible.

Finally, the presence of the three heat conducting elements does not impose any limitation on the types and styles of the perfume diffuser or the perfume diffusing system including it.

In an advantageous version of the invention, the heat conducting elements are adapted and dimensioned to transmit to the substance by thermal conduction a flow of heat sufficient to heat said substance to a substantially constant temperature in the range from approximately 40° C. to approximately 65° C.

In this way it is possible to achieve a speed of diffusion and an intensity of the perfume that are substantially constant and which correspond to the requirements of users.

A perfume diffuser of the above kind perfumes the environment by sublimation or evaporation of a perfume or a perfumed substance (liquid, solid or gel) using a thermally conducting system forming an integral part of the perfume or perfumed substance. In order to operate, this thermal system necessitates the use of a flame or other sources of heat and transmits a predetermined quantity of heat to the perfumed substance by thermal conduction that is sufficient for the latter to evaporate or sublimate with a relatively regular speed of diffusion. The capacity of the reservoir is preferably sufficient to enable continuous operation for several hours (for example, the life of a candle), without obliging the user to refill it frequently. The range of temperature used enables perfumes to be chosen from a wide range of fragrant substances, including the lightest ones, which evaporate at the lowest temperatures, from 40° C., without any limitation being created by insufficient control of the temperature of the substance to be diffused.

In a preferred version of the invention, the third conducting element has a transverse dimension that increases in the direction towards the second element at least in the portion of said element which is in contact with the perfumed substance.

As the substance adapted to diffuse the perfume is used up, the length of the portion of said element that is in contact with the substance decreases and its width increases. This maintains a substantially constant ratio between the area of thermal exchange between the second and third heat conducting elements, on the one hand, and the volume of the substance adapted to diffuse the perfume, to maintain sufficient heat input to maintain a substantially constant temperature of said substance and a substantially constant state of diffusion of the perfume.

In accordance with another aspect of the invention, a system for diffusing a perfume in accordance with the invention, including a heat source and a container containing a substance adapted to diffuse a perfume on evaporating or sublimating, is characterized in that it includes a perfume diffuser in accordance with the first version of the present invention.

Other features and advantages of the present invention will become apparent in the following detailed description.

BRIEF DESCRIPTION OF THE DRAWINGS

In the accompanying drawings, which are given by way of non-limiting example only:

FIG. 1 is a diagrammatic elevation view showing the structure of a system for diffusing a perfume in accordance with the second aspect of the invention, comprising a perfume diffuser in accordance with one embodiment of the first aspect of the present invention;

FIG. 2 is a view of the embodiment of the perfume diffuser shown in FIG. 1 in elevation and in section taken along the line II—II in FIG. 4;

FIG. 3 is a view of the perfume diffuser from FIG. 2 as seen from the left in that figure;

FIG. 4 is a plan view of the perfume diffuser from FIG. 2;

FIG. 5 is a diagram representing two variants of the system from FIG. 1; and

FIG. 6 is a diagram showing the evolution with time of the diffusion of a perfume for a system for diffusing a perfume or a perfumed substance and a perfume diffuser in accordance with the present invention.

DETAILED DESCRIPTION OF THE PREFERRED EMBODIMENT(S)

In the embodiment shown diagrammatically in FIG. 1, the system 1 for diffusing a perfume or a perfumed substance includes a heat source 2 and a container 3 containing a substance 4 adapted to diffuse a perfume on evaporating or sublimating.

The heat source 2 is conventionally a small candle comprising a combustible product 5 and a wick 6 adapted to become impregnated with the combustible product 5, for example. When the candle 2 is lit, it produces a flame 7 which gives off heat.

The container 3 is a container of any shape, made of any substance and adapted to contain the substance 4 and to withstand the temperature to which the substance is heated.

The substance 4 adapted to diffuse a perfume on evaporating or sublimating is any substance known per se in the form of a liquid, solid or gel. To eliminate all risk of fire, the substance 4 is usually an aqueous substance in liquid, solid or gel form containing a perfumed substance adapted to be diffused when the substance 4 evaporates or sublimates.

The system 1 includes an embodiment of a perfume diffuser 8 in accordance with the invention shown in detail in FIGS. 2 to 4.

In the embodiment shown in FIGS. 2 to 4, the perfume diffuser 8 is adapted to cooperate with a heat source 2 and with means adapted to receive or to constitute a container 3 containing a substance 4 adapted to diffuse a perfume on evaporating or sublimating. The diffuser 8 and the aforementioned means are adapted to transmit to the substance 4 a portion of the heat produced by the heat source 2.

In accordance with the present invention, the perfume diffuser 8 includes:

a first heat conducting element 9, possibly with its outside surface thermally insulated, adapted to receive a portion of the heat produced by said source 2 of heat and to transmit the heat received by thermal conduction;

a second heat conducting element 10 separated from the first element 9 and adapted to be in contact with said substance 4;

a third heat conducting element 11, possibly with its outside surface thermally insulated from the tongue 9 and over substantially all of its height exposed to the air (see below), connected to the first conducting element 9 and to the second conducting element 10 so as to communicate the heat transmitted by the first conducting element 9 to the second conducting element 10 by thermal conduction.

The heat conducting elements 9, 10, 11 are adapted and dimensioned to transmit a sufficient flow of heat to the substance 4 by thermal conduction to heat said substance 4 to a substantially constant temperature in the range from approximately 400° C. to approximately 65° C.

The temperature range from approximately 40° C. to approximately 65° C. is known to be the ideal range for diffusing a perfume.

As shown in the figures, the three heat conducting elements 9, 10, 11 are made in one piece, the perfume diffuser 8 being made principally of a metal that is a good conductor of heat and resistant to the temperature created by the source 2, for example aluminum, copper or any other suitable metal. Other embodiments are possible.

In the example shown, the perfume diffuser 8 is made from sheet metal cut and bent to shape, for example from sheet aluminum or copper approximately 1 mm thick. The diffuser 8 could be molded or cast or pressed.

In the example shown, the perfume diffuser 8 is adapted to cooperate with a heat source 2 consisting of a flame 7, for example the flame 7 of a candle.

The first heat conducting element 9 is a metal tongue 9 inclined to the direction of the flame 7, i.e. the vertical direction, and possibly touching the end of the flame 7 when the diffuser 8 is operating. The tongue 9 is therefore at the top of the diffuser 8.

The tongue 9 is preferably formed so that its inclination relative to the direction of the flame 7 is adjustable (see below).

More generally, the perfume diffuser 8 includes means, described in detail hereinafter, for modifying the distance between the tongue 9 and the flame 7 in order to adjust the speed of diffusion of the perfume.

The second heat conducting element 10 is adapted to be embedded in the substance 4 and the third conducting element 11 has a portion 12 adjacent the second conducting element 10 also adapted to be embedded in the substance 4.

The second heat conducting element 10 covers substantially all of the surface of the bottom 13 of the container 3 containing the substance 4 (see FIG. 1).

The second heat conducting element 10 rests on the bottom 13 of the container 3 containing the substance 4, either directly or via spacers 14 that hold it at a distance from said bottom 13 to increasess the area of thermal exchange between the second conducting element 10 and the substance 4.

In the example shown in FIGS. 2 to 4 the second element 10 has a substantially circular shape that is easily inscribed within the cross section of the container 3, which can have any shape. It is at the bottom of the diffuser 8.

Said element 11 has a transverse dimension that increases in the direction towards the second element 10, at least in the portion 12 of the third conducting element 11 which is adapted to be in contact with the substance 4.

In the example shown, the third conducting element 11 serves as an upright for supporting the tongue 9, which is linked to the upright 11 by the bend 15 and the tray 16 adapted to support the candle 2 or other heat source under the tongue 9.

The tray 16 is adjustably fixed to the upright 11 by means of a bolt 17 passing through a vertical longitudinal slot 18 in the upright 11, a washer 19 being inserted between the head of the bolt 17 opposite the tray 16 and the upright 11.

Initial experiments by the Applicant show that it would appear to be very important for at least the portion 12 of the upright 11 adjacent the second conducting element 10 to have a transverse dimension that widens in the direction towards the second element 10. This increases the ratio between the total area of thermal exchange between the diffuser 8 and the substance 4, on the one hand, and the residual height of the substance 4 in the container 3, and thus the residual volume of the substance 4 in said container 3, on the other hand. This achieves a substantially constant speed of diffusion of the perfume despite the progressive disappearance of the substance 4 and the reduction in its level and the volume.

For this reason, the upright 11 can have a regular trapezoidal shape, as shown in FIG. 3. The lower part 12 of the upright 11 adapted to dip into the substance 4 can also have lateral wings 20, shown diagrammatically in dashed outline in FIGS. 3 and 4, which can have any shape and orientation and which can lie either in the plane of the upright 11 or along a curved surface shown diagrammatically in the bottom part of FIG. 4, for example.

In the embodiment shown in FIG. 5, the candle 2 placed on a tripod 21 resting directly under the second element 10 is shown in continuous line: the candle 2 is therefore above the second element 10 and below the tongue 9, without being supported by the upright 11. This figure also shows in dashed outline a variant in which the candle 2 is supported by a support 22 cantilevered from the container 3, the tongue 9 being bent towards the exterior of the container so that it lies above the support 22.

To adjust the distance between the tongue 9 and the heat source 2, 7, for example to allow for the reducing height of a candle 5 as it burns down, the angle of the tongue 9 relative to the upright 11 can be adjusted by bending the tongue 9 towards the flame 7 at the bend 15. It is bent in the opposite direction when replacing a spent candle with a new one.

Means can equally be provided with the tongue 9 causing it to bend automatically towards the flame 7 when the temperature of the tongue 9 falls. Thus the tongue 9 can be associated with an auxiliary tongue 23 welded at its ends to the tongue 9 to constitute a bimetallic strip, the position and the nature of the metal of the tongue 23 being chosen to achieve the required result, a device of this kind operating in both directions.

Accordingly, as shown diagrammatically in FIG. 1, the tongue 23a can be placed under the tongue 9 if it is made of a metal that contracts faster than the metal of the tongue 9 as the temperature falls. A tongue 23b of a metal contracting slower than that of the tongue 9 would be situated on top of the latter.

As an alternative, the upright 11 can be designed with a bimetallic strip structure in order to move the tongue 9 relative to the flame 7.

The tongue 9 and the upright 11 are thermally insulated over at least a portion of their outside surface to limit heat losses by radiation from the diffuser 8 and to communicate to the base 10 and to the perfumed substance 4 a maximum proportion of the quantity of heat received by the tongue 9.

The outside surface of the tongue 9 opposite the flame 7 is coated with a thermally insulative coating 24 in the example shown.

Similarly, at least the outside face of the upright 11 is coated with an insulative coating 24, substantially above the level of the tray 16. In this way, the bottom part 12 likely to come into contact with the perfumed substance 4 remains bare to allow optimum thermal exchange with the latter.

Of course, the coating 24 can also be designed as a decorative coating or covered with a decorative coating of any kind.

A perfume diffuser has therefore been described with has an extremely simple and therefore very economical structure which lends itself to all possible embodiments; if the heat source is a flame, for example a candle flame, the perfume diffuser 8 enables the flame to be seen so that the flame contributes to creating a warm atmosphere, especially after dark. The diffuser receives heat energy at the temperature of the flame via the tongue 9 and transmits to the perfumed substance 4 heat energy at a substantially lower temperature, in the required range from approximately 40° C. to approximately 65° C.

Surprisingly, the perfume diffuser in accordance with the invention achieves a relatively constant speed of diffusion of perfume by evaporation. This is seen in FIG. 6 which represents a curve of the evolution of the diffusion of a perfume during a test carried out under the conditions specified below. The test lasted approximately 51 hours and gave the following results:

| Duration of use of system (h) | Total loss of perfume (g) | Average hourly consumption of perfume (g/h) |
| --- | --- | --- |
| 3 | 2.84 | 0.95 |
| 7 | 7.3 | 1.04 |
| 10.8 | 11.31 | 1.05 |
| 14.5 | 15.35 | 1.06 |
| 18.3 | 18.76 | 1.02 |
| 22.3 | 23.1 | 1.04 |
| 26.5 | 27.72 | 1.05 |
| 30.5 | 34.01 | 1.12 |
| 34.7 | 37.61 | 1.09 |
| 39.7 | 42.06 | 1.06 |
| 43.4 | 46.59 | 1.07 |
| 47.2 | 49.7 | 1.05 |
| 50.9 | 53.5 | 1.05 |

The tests were carried out with a system as shown in FIGS. 1 to 4 and a diffuser approximately 8 cm high, the heat source being a candle.

The total loss of perfume is the total loss of weight at time t from the start of the experiment and corresponds to the lefthand scale in FIG. 6.

The average hourly consumption is the total loss of perfume at time t divided by the number of hours since the start of the experiment and corresponds to the righthand scale in FIG. 6.

Of course, the present invention is not limited to the embodiments just as described, to which many changes and modifications can be made without departing from the field of the invention.

In particular, the flame described can be replaced by any other heat source. Thus a magnifying glass can be used to concentrate the rays of the sun to heat the conducting tongue 9, or a source of infrared radiation can be used for this purpose. The heat source 2 can be placed in any position relative to the substance 4.

Of course, the quantity of heat transmitted by conduction to the perfumed substance is not strictly equal to the quantity of heat received by the first conducting element, given that losses occur by conduction, radiation and convection from the various conducting elements. These losses can vary as a function of parameters of the atmosphere in which the diffuser is installed, the temperature, the relative humidity, the degree of agitation of the surrounding air. These losses also vary as the area of contact between the conducting elements and the perfumed substance varies as said substance is used up.

The heat source can of course be placed on a support independent of the conducting elements to provide more than one heat source associated with one or more sets of conducting magnets.

The second conducting element adapted to be in contact with the perfumed substance can have any shape compatible with its function. In particular, the two wings 20 can have substantially the shape of two semi-cylinders with the same axis and a predetermined diameter so that the wings bear elastically against the walls of the container containing the perfumed substance and provide a large area of thermal exchange with said substance, if necessary in association with a bottom element 10, the bottom of the container having any non-plane shape.

The burning conducting elements can advantageously be protected by an insulative substance, in particular of the porous ceramic type; they can be embedded in a substance of this kind, for example, or surrounded by a sheath of such a substance.

The combination of the first, second and third conducting elements can have a more or less stylized general shape in elevation, for example the shape of a numeral, such as 2, 3, 5, 6, 8 or 9 or a letter, such as A, B, C, E, G, O or θ, P, R, S, Z, d, b, a. The heat source can if required be deposited on a horizontal part of the shape or added thereto. In particular, by virtue of the oblique transverse bar, the Z shape offers an exchange area that decreases relatively little as the height of the perfumed substance decreases.

Most of the shapes mentioned above can be obtained by cutting and bending sheet metal.

It is also possible to form and stamp sheet metal on a press. Thus in a variant of the two semi-cylindrical wings described above, the second conducting element can be designed as a substantially cylindrical container adapted to contain the perfumed substance directly and fabricated on a press, the first and second conducting elements in accordance with the present invention being associated in any manner with this container, preferably being in one piece with it.

The container obtained in this way, which of itself provides all the technical functions of the perfume diffuser in accordance with the present invention, is adapted to be introduced into an enclosure or a container of any shape which can be designed in accordance with essentially economic and esthetic criteria.

The diffuser can equally be made by molding or casting any appropriate substance.

The diffuser of the invention can also be made from substances which are a good conductor of heat other than metals, for example glass or any other substance, especially a vitreous substance, resistant to the temperature of the flame or heat source. The dimensions of the various conducting elements forming the diffuser are then such that they fulfil the functions described hereinabove for the diffuser, and in particular communicate to the perfumed substance the quantity of heat necessary to heat it to the required temperature.

What is claimed is:

1. A perfume diffuser adapted to cooperate with a source of heat and with means for receiving or constituting a container for a perfumed substance adapted to diffuse a perfume upon evaporation or sublimation, the diffuser and said means transmitting to said perfumed substance a portion of the heat produced by said heat source, said diffuser comprising:

a first heat conducting element separated from and at a distance from said means, said first heat conducting element receiving a portion of the heat produced by said heat source and transmitting a portion of the heat received by thermal conduction;

a second heat conducting element separated from and at a distance from the first heat conducting element, said second heat conducting element being in contact with said perfumed substance;

a third heat conducting element connected to the first heat conducting element and to the second heat conducting element, said third heat conducting element communicating a portion of the heat transmitted by the first heat conducting element to the second heat conducting element by thermal conduction;

the first and third heat conducting elements each having an outside surface, and at least one of the first and third heat conducting elements being optionally thermally insulated over at least a portion of its outside surface; and the perfumed substance receiving only heat received from the heat source by the first heat conducting element and transmitted by thermal conduction by said first heat conducting element to the third heat conducting element and then by said third heat conducting element to the second heat conducting element.

2. A perfume diffuser according to claim 1 wherein the first, second and third heat conducting elements are adapted and dimensioned to transmit to the perfumed substance by thermal conduction a flow of heat sufficient to heat said perfumed substance to a substantially constant temperature in the range from approximately 40° C. to approximately 65° C.

3. A perfume diffuser according to claim 1 wherein the first, second and third heat conducting elements are made in one piece.

4. A perfume diffuser according to claim 1 wherein said diffuser is made principally of a metal that is a good conductor of heat and resistant to the temperature created by the heat source.

5. A perfume diffuser according to claim 4 wherein said metal is selected from the group consisting of aluminum and copper.

6. A perfume diffuser according to claim 1 wherein said heat source consists of a flame and wherein said diffuser cooperates with said heat source and is characterized in that the first heat conducting element comprises a tongue inclined to the direction of the flame.

7. A perfume diffuser according to claim 6 wherein said tongue touches an end of said flame when the diffuser is operating.

8. A perfume diffuser according to claim 6 wherein the inclination of the tongue relative to the direction of the flame is adjustable.

9. A perfume diffuser according to claim 6 further comprising means for modifying the distance between the tongue and the flame.

10. A perfume diffuser according to claim 9 wherein said modifying means comprises a bimetallic strip.

11. A perfume diffuser according to claim 6 wherein the second heat conducting element is embedded in the perfumed substance and the third conducting element has a portion adjacent the second conducting element which is also embedded in said perfumed substance.

12. A perfume diffuser according to claim 11 wherein the second heat conducting element extends over substantially all of a bottom surface of the container containing the perfumed substance.

13. A perfume diffuser according to claim 11 characterized in that the second heat conducting element rests on spacers on a bottom of the container containing the perfumed substance which spacers hold said second heat conducting element at a distance from said bottom.

14. A perfume diffuser according to claim 11 further comprising at least the portion of the third heat conducting element which is in contact with the perfumed substance has a transverse dimension that increases in a direction toward the second heat conducting element.

15. A system for diffusing a perfume including a heat source, a container containing a perfumed substance adapted to diffuse a perfume on evaporating or sublimating, and a perfume diffuser, said perfume diffuser including first heat conducting element separated from and at a distance from said means, said first heat conducting element receiving a portion of the heat produced by said heat source and transmitting a portion of the heat received by thermal conduction; a second heat conducting element separated from and at a distance from the first heat conducting element, said second heat conducting element being in contact with said perfumed substance; a third heat conducting element connected to the first heat conducting element and to the second heat conducting element, said third heat conducting element communicating a portion of the heat transmitted by the first heat conducting element to the second heat conducting element by thermal conduction; the first and third heat conducting elements each having an outside surface, and at least one of the first and third heat conducting elements being optionally thermally insulated over at least a portion of its outside surface; and the perfumed substance receiving only heat received from the heat source by the first heat conducting element and transmitted by thermal conduction by said first heat conducting element to the third heat conducting element and then by said third heat conducting element to the second heat conducting element.

* * * * *